United States Patent
Ben Arous et al.

(10) Patent No.: US 9,889,196 B2
(45) Date of Patent: Feb. 13, 2018

(54) ADJUVANTED VACCINES FOR IN OVO AVIAN VACCINATION

(71) Applicant: SOCIETE D'EXPLOITATION DE PRODUITS POUR LES INDUSTRIES CHIMIQUES SEPPIC, Paris (FR)

(72) Inventors: Juliette Ben Arous, Issy les Moulineaux (FR); Laurent Dupuis, Reims (FR); Hyun Lillehoj, Beltsville, MD (US)

(73) Assignee: SOCIETE D'EXPLOITATION DE PRODUITS POUR LES INDUSTRIED CHIMIQUES SEPPIC, Paris (FR)

( * ) Notice: Subject to any disclaimer, the term of this patent is extended or adjusted under 35 U.S.C. 154(b) by 0 days.

(21) Appl. No.: 15/033,793

(22) PCT Filed: Nov. 12, 2014

(86) PCT No.: PCT/FR2014/052874
§ 371 (c)(1),
(2) Date: May 2, 2016

(87) PCT Pub. No.: WO2015/071586
PCT Pub. Date: May 21, 2015

(65) Prior Publication Data
US 2016/0256544 A1    Sep. 8, 2016

(30) Foreign Application Priority Data
Nov. 12, 2013 (FR) ..................... 13 60999

(51) Int. Cl.
*A61K 39/00* (2006.01)
*A61K 39/02* (2006.01)
*A61K 39/08* (2006.01)
*A61K 39/39* (2006.01)
*A61K 39/012* (2006.01)
*A61K 39/002* (2006.01)

(52) U.S. Cl.
CPC ............ *A61K 39/39* (2013.01); *A61K 39/002* (2013.01); *A61K 39/012* (2013.01); *A61K 39/08* (2013.01); *A61K 2039/54* (2013.01); *A61K 2039/552* (2013.01); *A61K 2039/55566* (2013.01)

(58) Field of Classification Search
CPC ....................................... A61K 39/39
See application file for complete search history.

(56) References Cited

U.S. PATENT DOCUMENTS

| | | | | |
|---|---|---|---|---|
| 5,273,901 A * | 12/1993 | Jacobson | ............ | C07K 14/455 424/191.1 |
| 2006/0233825 A1* | 10/2006 | Jayappa | ................ | A61K 39/08 424/190.1 |
| 2007/0243212 A1 | 10/2007 | Doelling et al. | | |
| 2008/0187552 A1 | 8/2008 | Aucouturier et al. | | |
| 2012/0321663 A1 | 12/2012 | Bertrand et al. | | |
| 2013/0011434 A1 | 1/2013 | Bertrand et al. | | |

FOREIGN PATENT DOCUMENTS

| | | |
|---|---|---|
| EP | 1 095 662 A1 | 5/2001 |
| WO | 2011/117506 A2 | 9/2011 |
| WO | 2011/117507 A1 | 9/2011 |

OTHER PUBLICATIONS

International Search Report, dated Feb. 18, 2015, from corresponding PCT/FR2014/052874 application.

* cited by examiner

*Primary Examiner* — Albert M Navarro
(74) *Attorney, Agent, or Firm* — Young & Thompson

(57) ABSTRACT

A composition includes at least one mineral oil, a surfactant having a hydrophilic property characterized by an HLB value equal to 12 and a divalent inorganic salt intended to be used as an adjuvant in a vaccine composition for the in ovo vaccination of avian species wherein the composition is an oil-in-water emulsion or microemulsion.

12 Claims, 2 Drawing Sheets

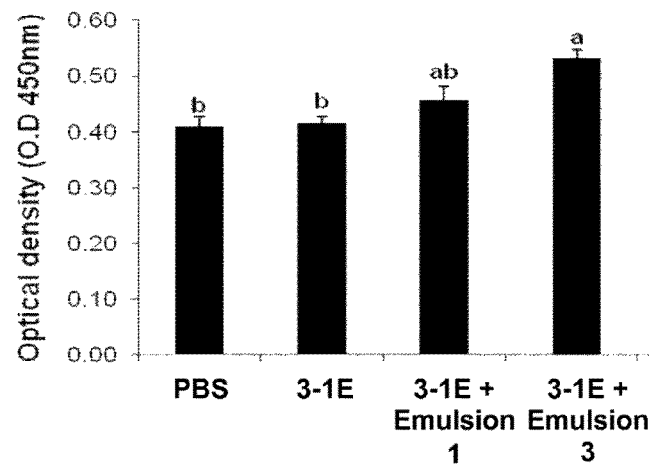
Figure 1: Anti-3-1E serum antibodies at D18 post-vaccination, before infection
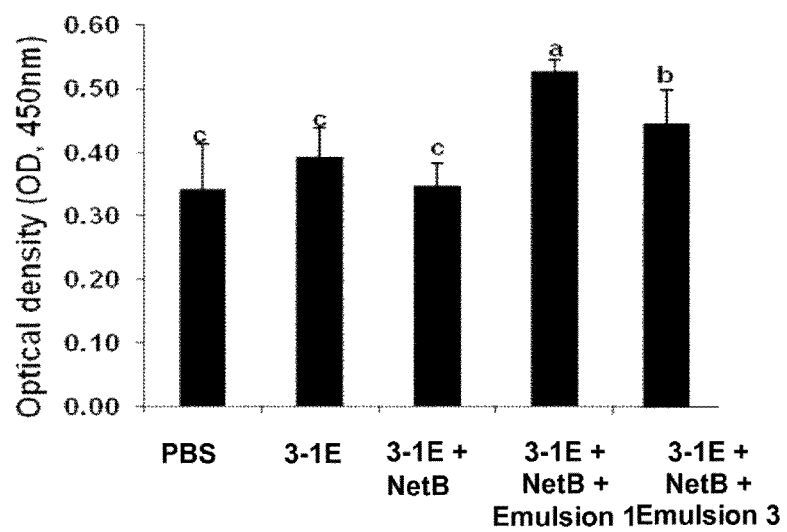
Figure 2: Anti-NetB serum antibodies at D18 post-vaccination, before infection

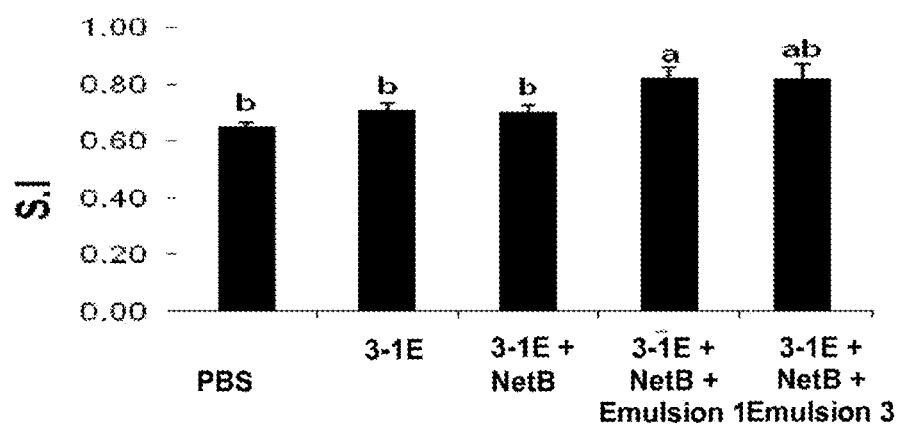
Figure 3: Index for specific stimulation of splenocytes by the NetB antigen at 16 days after vaccination

ADJUVANTED VACCINES FOR IN OVO AVIAN VACCINATION

The present invention relates to the use of adjuvants for formulating vaccine compositions intended for the prevention of avian diseases and intended to be applied by in ovo administration (injection into the egg), said adjuvant comprising at least one oily phase and at least one pharmaceutically acceptable divalent inorganic salt.

A vaccine adjuvant is an excipient which amplifies the immunological response against the antigen of the vaccine with which it is combined. These adjuvants are diverse in nature. They may equally consist of liposomes, of emulsions comprising at least one oil phase and at least one aqueous phase, such as "Freund's" adjuvants, of adjuvants of biological origin (cytokines, oligonucleotides, etc.) or of water-insoluble mineral salts. Among the mineral salts used as vaccine composition adjuvants, mention may, for example, be made of aluminum hydroxide, which is very commonly used. For the formulation of vaccine compositions containing an inactivated antigen and intended for injection of avian species, adjuvants of water-in-oil emulsion type are predominantly used.

The use of adjuvants in vaccine compositions makes it possible in particular:

to increase the strength of the protective response conferred by a dose of vaccine, making it possible to provide a better level of protection;

to prolong the duration of the protection conferred by a dose of vaccine, providing longer-lasting protection of animals on farms throughout their growth;

to obtain, with a lower dose of antigen, an efficacy equivalent to that conferred by a complete dose used without adjuvant. Thus, a vaccine production entity will, with the same productive capacity, be capable of producing a large number of vaccine doses. Likewise, an existing conditioning may be proposed for vaccinating a larger number of animals;

to reduce the number of immunizations required in order to provide vaccine protection.

The prevention of infectious avian diseases of viral, bacterial or parasitic origin is essential for supporting the development of poultry production. Vaccination is a recommended method for preventing a large number of diseases of avian species, such as Newcastle disease, avian flu, Gumboro disease, Marek's disease, coccidiosis, infectious bronchitis, fowl cholera, etc. Broiler chickens live at most a few months and receive multiple vaccines during their life, in particular during their first days.

Avian vaccines can be administered by subcutaneous or intramuscular injection in the chick or the adult, mucosally (orally, intranasally, intraocularly), by mass administration (nebulization or administration in the drinking water), or by injection into the egg when the embryo reaches 18 or 19 days after fertilization (in ovo administration).

Vaccination via an injectable route is conventionally used to administer avian vaccines. However, since the vaccination of a very large number of animals represents high labor costs under intensive farming conditions, new methods have been developed more recently. In ovo vaccination is thus a method of vaccine administration which is increasingly advocated, since it is directly applicable in breeding establishments (hatcheries), and which allows considerable reductions in cost and time devoted to vaccination.

The antigens devoted to avian vaccine compositions may consist of killed pathogens (inactivated vaccines), live pathogens in which the virulence has been reduced (live attenuated vaccines), recombinant immunogenic proteins (subunit vaccines) or recombinant live vectors (vector vaccines). Live attenuated vaccines and vector vaccines are generally effective enough not to require the systematic addition of adjuvants, even though it is possible to amplify the efficacy of live vaccines using suitable adjuvants, as described, for example, in patent application WO 2011/117507. Conversely, the formulation of inactivated and subunit vaccines generally requires the addition of immune adjuvant in order to achieve the required vaccine efficacy.

The commercial vaccines currently administered in ovo are live attenuated vaccines not containing adjuvant. Since live attenuated vaccines can have risks of virulence reversion, the development of inactivated or subunit vaccines for in ovo vaccination is advantageous. However, the avian vaccine compositions containing an inactivated or subunit antigen and an oily adjuvant of water-in-oil type, which are very widely used for administration by injection in chicks or adults, cannot be used as they are for in ovo administration. This is because the oily adjuvants generally used for vaccinating chicks and adults are toxic to the development of the embryo in the egg. The development of a specific adjuvant which allows the use of inactivated antigens in ovo is therefore required.

An adjuvant intended for in ovo administration must therefore have the following specific characteristics:

be nontoxic to the development of the avian embryo;

be compatible with live attenuated (nonvirucidal) vaccines;

increase the protection conferred by the vaccine antigen, according to the modes previously described.

Various adjuvant technologies have already been tested for in ovo vaccination, such as aluminum hydroxide salts, polymers of carbomer type, adjuvants of biological origin, such as CPGs, cytokines and chemokines, and saponin. However, there is no consensus and the development of new effective adjuvant formulations at a cost compatible for in ovo vaccination remains necessary.

With regard to avian vaccines which are injectable in chicks or adults, the most effective adjuvant technologies are water-in-oil emulsions composed of an aqueous phase and an oily phase based on a mineral oil. No adjuvant based on oily emulsions has, however, been found to be effective for in ovo vaccination thus far, in particular owing to toxicity problems.

It has previously been shown that adjuvants of oil-in-water emulsion or microemulsion type are compatible with live vaccines and can be used as immune adjuvants for live vaccines (patent application WO 2011/117507). However, among these technologies, it has been shown that most of the adjuvants of this family are toxic to embryonic development in the egg.

Consequently, there is a need to use adjuvants containing an oil-in-water emulsion having the required characteristics, such as:

not being toxic to the embryonic development of the chicks;

being capable of increasing the protection given by a subunit antigen dedicated to avian vaccination administered in ovo.

A subject of the present invention is therefore a composition comprising at least one mineral oil, a surfactant having a hydrophilic nature characterized by an HLB value equal to 12 and a divalent inorganic salt intended to be used as an adjuvant in a vaccine composition for the in ovo vaccination of avian species, characterized in that said composition is an oil-in-water emulsion or microemulsion.

Moreover, embodiments of the invention may comprise one or more of the following characteristics:

A composition as defined above, comprising, for 100% of its weight:
- from 50% to 97% of water, more particularly from 70% to 97% of water, and even more particularly from 80% to 97% of water;
- from 1% to 45% of oily adjuvant, more particularly from 1% to 30% of oily adjuvant, and even more particularly from 2% to 10% of oily adjuvant;
- from 0.1% to 10% of at least one divalent inorganic salt, more particularly from 0.1% to 8%, and even more particularly from 0.2% to 3%;
- from 0% to 10% of at least one complexing agent, more particularly from 0% to 8%, and even more particularly from 0% to 3%.

A composition as defined above, characterized in that said oily adjuvant comprises, for 100% of its weight:
- from 40% to 95% of at least one mineral oil, more particularly from 50% to 95% of at least one mineral oil, and even more particularly from 50% to 90% of at least one mineral oil;
- from 5% to 60% of at least one surfactant, more particularly from 5% to 50% of at least one surfactant, and even more particularly from 10% to 50% of at least one surfactant.

A composition as defined above, characterized in that said at least one divalent inorganic salt is chosen from manganese gluconate, calcium gluconate, calcium aspartate, zinc gluconate, iron gluconate and calcium chloride.

A composition as defined above, characterized in that said at least one complexing agent is chosen from ethylenediaminetetraacetic acid (EDTA), sodium gluconate, potassium gluconate and sodium polyacrylate.

A composition as defined above, characterized in that the surfactant is an ethoxylated sugar ester.

A composition as defined above, characterized in that the mineral oil is a white liquid petroleum jelly of injectable quality.

According to another aspect, a subject of the invention is a vaccine composition intended for the in ovo vaccination of avian species, comprising at least one antigen and an immune adjuvant composition as defined above.

Moreover, embodiments of the invention may comprise one or more of the following characteristics:

A composition as defined above, characterized in that the antigen contains at least one recombinant subunit protein.

A composition as defined above, characterized in that said subunit protein is a protein from *Eimeria*, more particularly from *Eimeria acervulina* and more particularly profilin 3-1E, for the purpose of protection against avian coccidiosis.

A composition as defined above, characterized in that said subunit protein is a protein from *Clostridium perfringens*, more particularly the NetB toxin, or the alpha toxin, or the proteins pyruvate: ferredoxin oxidoreductase (PFO), or elongation factor Tu (EF-Tu), for the purpose of protection against necrotic enteritis.

A composition as defined above, characterized in that said antigen contains at least one protein from *Clostridium perfringens*, more particularly the NetB toxin, or the alpha toxin, or the proteins pyruvate: ferredoxin oxidoreductase (PFO), or elongation factor Tu (EF-Tu), and a protein from *Eimeria*, more particularly from *Eimeria acervulina* and more particularly profilin 3-1E, for the purpose of protection against avian coccidiosis and avian necrotic enteritis.

A composition as defined above, comprising at least one antiparasitic live antigen of coccidiosis.

A composition as defined above, comprising at least one live antigen used in avian vaccinations.

The term "microemulsion" is understood to mean a thermodynamically stable dispersion of two immiscible liquids, stabilized by one (or more) surfactant(s). These dispersions are generally transparent since the typical sizes of the mesophases are less than the wavelength of light, and often nanometric.

An example is given by the aqueous dispersion of small droplets of oils stabilized by surfactants. By virtue of their diameter (a few tens of nanometers), they are invisible to the naked eye and even under a microscope. Their size can be measured by microscopic techniques such as small angle radiation scattering.

The emulsions or microemulsions which are the subject of the present invention have a color on the macroscopic scale over a range of from bluish to white.

The mineral oils used for preparing the oily adjuvants are selected from the group made up of mineral oils, hydrocarbons, obtained by distillation of petroleum and by the implementation of subsequent processing steps such as, for example, desulfurization, deasphalting, aromatic compound extraction and wax extraction steps, and other finishing processing steps (mention may, for example, be made of oils of the Marcol 52, Marcol 82, Drakeol 5, Drakeol 6, Eolane 170, etc., type).

The surfactants present in the oily adjuvants are emulsifying surfactants having a hydrophilic nature characterized by an HLB value of between 8 and 15. Preferably, its HLB value is equal to 12. Such a surfactant may consist of an alkylpolyglycoside or a mixture of alkylpolyglycosides; saponins; lecithins; polyethoxylated alkanols; polymers comprising polyoxyethylene and polyoxypropylene blocks; esters obtained by condensation of a fatty acid, advantageously a fatty acid that is liquid at 20° C., with a sugar, sorbitol, mannitol or glycerol. Said sugar may consist of glucose or sucrose or, preferably, mannitol. By way of preferred esters, mention may be made of esters of fatty acids, for instance oleic acid, stearic acid, palmitic acid or lauric acid, and of sorbitol or mannitol, obtained by esterification of the fatty acid with sorbitol or mannitol, or else by esterification with the products resulting from the anhydrization of the polyhydroxylated chain of sorbitol or of mannitol which cyclizes in position 1-4 or in position 2-6, or else by esterification with sorbitol or mannitol and with the products resulting from the anhydrization of the polyhydroxylated chain of sorbitol or of mannitol which cyclizes in position 1-4 or in position 2-6. As particularly preferred mannitol esters, mention may be made of mannitol oleates, mannitan oleates, ethoxylated mannitol oleates comprising 5 mol or 10 mol or 15 mol or 20 mol of ethylene oxide, and ethoxylated mannitan oleates comprising 5 mol or 10 mol or 15 mol or 20 mol of ethylene oxide. Polyethylene glycol, sorbitol or glycerol sugar ester derivatives may also be used. The other types of preferred surfactants consist of ethoxylated vegetable oils, for instance ethoxylated corn oils having between 3 mol and 40 mol of ethylene oxide, ethoxylated rapeseed oils having between 3 mol and 40 mol of ethylene oxide, or ethoxylated castor oils having between 3 mol and 60 mol of ethylene oxide.

The invention will be understood more clearly from the viewpoint of the examples and figures hereinafter.

EXAMPLES

Example 1: Compatibility of the Adjuvants with Avian Embryonic Development

In order to measure the compatibility of the adjuvants with the in ovo vaccination of chicken embryos, various adjuvants of oil-in-water emulsion type, compatible with various live attenuated vaccines, were formulated as placebo vaccines (aqueous phase: PBS). 0.1 ml of each of these placebo formulations was injected using an Intelliject injector (Avitech) and a 17.5 cm, 18-gage needle, in the amniotic cavity of 18-day fertilized eggs.

The toxicity is measured as the number of chicks hatched after injection with an adjuvanted placebo vaccine compared with the number of chicks hatched after injection with 0.1 ml of nonadjuvanted PBS. For comparison, a placebo based on a reference avian adjuvant of water-in-oil emulsion type, used to vaccinate adult chickens, was included in the test. Two series of trials were carried out, and the results are presented below.

Trial 1:

| Group | Adjuvant | Vaccine composition | Number of eggs injected | Number of chicks hatched | % hatching relative to the nonadjuvanted control |
|---|---|---|---|---|---|
| 1 | Nonadjuvanted | PBS | 25 | 13 | Reference 100% |
| 2 | Emulsion 1 | Mineral oil 1<br>Surfactant system 1<br>Divalent salt<br>% dry adjuvant: 12% | 25 | 15 | 115% |
| 3 | Emulsion 2 | Mineral oil 2<br>Surfactant system 1<br>Divalent salt<br>EDTA complexing agent<br>% dry adjuvant: 6% | 25 | 14 | 108% |
| 4 | Emulsion 3 | Mineral oil 1<br>Surfactant system 1<br>Divalent salt<br>EDTA complexing agent<br>% dry adjuvant: 12% | 25 | 14 | 108% |
| 5 | Emulsion 4 | Mineral oil 1<br>Surfactant system 2<br>Divalent salt<br>EDTA complexing agent<br>% dry adjuvant: 6% | 25 | 11 | 85% |
| 6 | Emulsion 5 | Mineral oil 1<br>Surfactant system 1<br>% dry adjuvant: 15% | 25 | 6 | 46% |
| 7 | Emulsion 6 | Mineral oil 2<br>Surfactant system 2<br>% dry adjuvant: 15% | 25 | 6 | 46% |
| 8 | Control: Water-in-mineral oil emulsion | % dry adjuvant: 70% | 25 | 8 | 62% |

Trial 2:

| Group | Adjuvant (% adjuvant/PBS) | Dose | Number of eggs injected | Number of chicks hatched | % hatching relative to the nonadjuvanted control |
|---|---|---|---|---|---|
| 1 | PBS/nonadjuvanted | 100 µl | 17 | 9 | — |
| 2 | Emulsion 1 | 100 µl | 17 | 12 | 133% |
| 3 | Emulsion 3 | 100 µl | 17 | 11 | 122% |
| 5 | Control: Water-in-oil emulsion | 100 µl | 16 | 5 | 55% |

Groups 2 to 5 use emulsions 1 to 4. In these compositions, the nonaqueous fraction represents, finally, in the vaccine prepared a percentage ranging from 6% to 12% (oil+surfactant+salts). Surfactant 1 is of the ethoxylated sugar ester family. Surfactant 2 is of the ethoxylated fatty alcohol family. Mineral oils 1 and 2 are white liquid petroleum jellies of injectable quality (for example: Marco 52® from Exxon). The divalent salt is a manganese salt or a calcium salt. The standard formula scheme is a base (mineral oil+surfactant HLB12) representing 10% to which are added 2% of salts in an aqueous solution qs 100%. These preparations make it possible to obtain a birth rate that is not significantly different than the group injected without adjuvant (group 1), indicating good tolerance. Groups 6 to 8, having similar qualitative and quantitative compositions, induce high mortalities (birth rate between 46% and 62%). These formulae are based on mixtures of oils+surfactants only.

Observation:
the number of chicks hatched is equivalent for groups 1 to 3. It is significantly lower for group 5.

In this trial, it is confirmed that emulsions of type 2 and 3 are compatible with in ovo vaccination since they induce no mortality; the W/O emulsion induces a high mortality and is not compatible with this application under the conditions tested.

These two trials show that only the adjuvants containing an emulsion and a pharmaceutically acceptable divalent salt are compatible with avian embryonic development.

Example 2: 1$^{st}$ Efficacy Trial: Model of Recombinant in Ovo Vaccine Against Coccidiosis The efficacy of the adjuvants selected after the innocuousness tests were then tested on a model of subunit vaccine against coccidiosis injected in ovo. Coccidiosis is an enteric parasitic avian disease caused by parasites of the *Eimeria* genus.

It was previously shown that vaccination by injection of chickens with a subunit vaccine adjuvanted using a waterin-oil adjuvant and comprising recombinant *Eimeria acervulina* profilin 3-1E as antigen made it possible to induce homologous protection against an *E. acervulina* infection and cross-protection against the other 2 major strains of *Eimeria* responsible for coccidiosis (*E. maxima, E. tenella*).

In this case, the antigen alone is not immunogenic enough to induce protection, and addition of the adjuvant is required [cf. S. I. Jang, H. S. Lillehoj, S. H. Lee, K. W. Lee, E. P. Lillehoj, F. Bertrand, L. Dupuis, S. Deville. Montanide™ ISA 71 VG adjuvant enhances antibody and cell-mediated immune responses to profilin subunit antigen vaccination and promotes protection against Eimeria acervulina and Eimeria tenella. Experimental Parasitology 127 (2011) 178-183. And also S. I. Jang, D. K. Kim, H. S. Lillehoj, S. H. Lee, K. W. Lee, F. Bertrand, L. Dupuis, S. Deville, J. Ben Arous, E. P. Lillehoj *Evaluation of Montanide™ ISA 71 VG Adjuvant during Profilin Vaccination against Experimental Coccidiosis*. PLoS ONE 8(4) (2013) e59786].

The *Eimeria acervulina* 3-1E antigen (50 µg/dose) was therefore combined with the adjuvants selected in the previous step for an in ovo injection.

The vaccination groups are presented below. 0.1 ml of each of these vaccines was injected using an Intelliject injector (Avitech) and a 17.5 cm, 18-gage needle, into the amniotic cavity of 18-day fertilized eggs.

| Group | Vaccine | Dose | Number of eggs injected | Number of chicks hatched | Infection |
|---|---|---|---|---|---|
| 1 | PBS | 100 µl | 15 | 14 | None |
| 2 | PBS | 100 µl | 15 | 13 | E.A. 10000 |
| 3 | Antigen 3-1E | 50 µg/100 µl | 15 | 11 | E.A. 10000 |
| 4 | Antigen 3-1E + Emulsion 1 | 50 µg/100 µl | 15 | 11 | E.A. 10000 |
| 5 | Antigen 3-1E + Emulsion 3 | 50 µg/100 µl | 15 | 12 | E.A. 10000 |

Observation: the number of chicks hatched is equivalent for groups 1 to 5.

After hatching, the chickens vaccinated in ovo are subjected to an infectious challenge 18 days post-vaccination (15 days after hatching) by inoculation in the esophagus with 10 000 sporulated oocytes of *Eimeria acervulina*. The resistance to infection is measured by recording the weight gain after infection, counting the oocytes excreted, measuring the intestinal lesions and the serological anti-profilin 3-1E response.

The results are analyzed statistically by ANOVA analysis. The differences are considered to be significant for $p<0.05$. Two significantly different values are represented by different letters.

Results:

1—Weight Gain:

The weight gain is measured between the day of infection and 10 days after infection:

| Group | PBS Non-infected | PBS Infected | Antigen Non-adjuvanted | Antigen + Emulsion 1 | Antigen + Emulsion 3 |
|---|---|---|---|---|---|
| Mean (g) | 752[a] | 672[c] | 683[c] | 730[b] | 700[c] |
| Standard deviation (g) | 35 | 51 | 45 | 34 | 31 |

2—Intestinal Lesions:

The score of the specific intestinal lesions caused by coccidiosis represents the mean of the scores given by three independent observers. The lesions are graded from 1 to 4, in increasing order of severity of the lesion.

| | PBS Infected | Antigen Nonadjuvanted | Antigen + Emulsion 1 | Antigen + Emulsion 3 |
|---|---|---|---|---|
| Mean score | 2.5[a] | 2.5[a] | 1.5[b] | 1.5[b] |
| Standard deviation | 0.58 | 0.58 | 0.58 | 0.58 |

3—Fecal Excretion of Oocytes:

The feces of each group were harvested between the 6th and 10th day after infection, and the *Eimeria* oocytes excreted after infection were counted.

| | PBS Infected | Antigen Nonadjuvanted | Antigen + Emulsion 1 | Antigen + Emulsion 3 |
|---|---|---|---|---|
| Mean ($\times 10^8$/animal) | 2.93[a] | 2.71[a] | 2.43[b] | 2.11[b] |
| Standard deviation | 0.47 | 0.24 | 0.24 | 0.41 |

4—Anti-3-1E Serum Antibodies:

The specific serum antibodies against profilin 3-1E were measured by taking a blood sample and performing an ELISA analysis before infection 18 days after immunization. The results are illustrated in FIG. 1.

Conclusion of the 1st Efficacy Trial:

The results obtained show that the adjuvants of oil-in-water emulsion type containing divalent salt, which may or may not be complex, are compatible with in ovo vaccination and increase the protection against coccidiosis conferred by a subunit antigen. The animals of the adjuvanted groups show, after infection, a higher weight gain, and parasite excretion and intestinal lesions which are reduced compared with the animals vaccinated with the nonadjuvanted antigen. They also show antigen-specific serum antibody titers which are higher than the animals vaccinated with the nonadjuvanted antigen. The nonadjuvanted vaccine does not allow any protection against coccidiosis.

Example 3: 2nd Efficacy Trial: Model of Bivalent Recombinant in Ovo Vaccine Against Coccidiosis and Necrotic Enteritis Secondly, the efficacy of the adjuvants selected was tested on a model of a bivalent subunit vaccine against coccidiosis and necrotic enteritis, injected in ovo.

Coccidiosis is an enteric parasitic avian disease caused by parasites of the *Eimeria* genus.

Necrotic enteritis is a bacterial enteric avian disease, caused by the bacterium *Clostridium perfringens*, and potentiated by the presence of a preinfection by *Eimeria*.

It was previously shown that vaccination by injection of chickens with an adjuvanted subunit vaccine comprising recombinant *Clostridium perfringens* NetB toxin as antigen made it possible to induce protection against *Clostridium perfringens* infection.

The NetB antigen alone is not immunogenic enough to induce protection, and the addition of an adjuvant is required [cf. S. I. Jang, H. S. Lillehoj, S. H. Lee, K. W. Lee, E. P. Lillehoj, Y. H. Hong, D. J. An, W. Jeong, J. E. Chun, F. Bertrand, L. Dupuis, S. Deville, J. Ben Arous—Vaccination with *Clostridium perfringens* recombinant proteins in combination with Montanide™ ISA 71 VG adjuvant increases protection against experimental necrotic enteritis in commercial broiler chickens. Vaccine 30 (2012) 5401-5406].

The *Eimeria acervulina* 3-1E antigen (50 µg/dose) and the *Clostridium perfringens* NetB antigen (50 µg/dose) were therefore combined with the selected adjuvants for an in ovo injection.

The vaccination groups are presented below. 0.1 ml of each of these vaccines was injected using an Intelliject injector (Avitech) and a 17.5 cm, 18-gage needle, in the amniotic cavity of 18-day fertilized eggs.

| Group | Vaccine | Dose | Number of eggs injected | Number of chicks hatched | Infection |
|---|---|---|---|---|---|
| 1 | PBS | 100 µl | 15 | 11 | None |
| 2 | PBS | 100 µl | 15 | 10 | EA 10 000 C.P 1 × 10$^9$ CFU |
| 3 | 3-1E Non-adjuvanted | 100 µl | 15 | 9 | EA 10 000 C.P 1 × 10$^9$ CFU |
| 4 | 3-1E + NetB Non-adjuvanted | 50 µg/100 µl | 15 | 7 | EA 10 000 C.P 1 × 10$^9$ CFU |
| 5 | 3-1E + NetB + Emulsion 1 | 50 µg/100 µl | 15 | 7 | EA 10 000 C.P 1 × 10$^9$ CFU |
| 7 | 3-1E + NetB + Emulsion 3 | 50 µg/100 µl | 15 | 7 | EA 10 000 C.P 1 × 10$^9$ CFU |

Observation:

the number of chicks hatched is considered to be equivalent for all the groups.

After hatching, the chickens vaccinated in ovo (5 chickens/group) are subjected to an infectious challenge at 18 days post-vaccination (15 days after hatching) by inoculation in the esophagus with 10 000 sporulated oocytes of *Eimeria acervulina*, then 3 days later (21 days after vaccination) to an infection with 10$^9$ CFU of *C. perfringens*.

The resistance to infection is measured by recording the weight gain after infection, measuring the intestinal lesions, the anti-NetB toxin serological response, and the splenocyte proliferation after restimulation with the NetB toxin.

The results are analyzed statistically by ANOVA analysis. The differences are considered to be significant for $p<0.05$. Two significantly different values are denoted by different letters.

Results:

1—Weight Gain:

The weight gain is measured between the day of infection with *Eimeria* (d18 post-vaccination) and 2 days after infection with *Clostridium* (d23 post-vaccination).

|  | PBS Infected | 3-1E Non-adjuvanted | 3-1E/NetB Non-adjuvanted | 3-1E/NetB Emulsion 1 | 3-1E/NetB Emulsion 3 |
|---|---|---|---|---|---|
| Mean (g) | 223 $^c$ | 231 $^c$ | 223 $^c$ | 245 $^b$ | 247 $^b$ |
| Standard deviation (g) | 31 | 31 | 17 | 27 | 22 |

2—Intestinal Lesions:

The score of the specific intestinal lesions represents the mean of the scores given by three independent observers. The lesions are graded from 1 to 4, in increasing order of severity of the lesion.

|  | PBS Infected | 3-1E Non-adjuvanted | 3-1E/NetB Non-adjuvanted | 3-1E/NetB Emulsion 1 | 3-1E/NetB Emulsion 3 |
|---|---|---|---|---|---|
| Mean score | 2.5 $^a$ | 2.5 $^a$ | 2.25 $^a$ | 1.5 $^b$ | 1.5 $^b$ |
| Standard deviation | 0.58 | 0.58 | 0.50 | 0.58 | 0.58 |

3—Anti-NetB Serum Antibodies:

The specific serum antibodies against the NetB toxin were measured by taking a blood sample and performing an ELISA analysis before infection with *E. acervulina* and *C. perfringens*, at d18 after vaccination. The results are illustrated in FIG. 2.

4—Specific Proliferation of Splenocytes by Restimulation with NetB:

The cellular response induced by the vaccination was measured by reproliferation of the lymphocytes of the spleen in the presence of NetB.

For 2 animals/group, the spleen was removed 16 days after immunization (before infection). The splenocytes were isolated and then restimulated in the presence of NetB for 48 h. The reproliferation is presented by a stimulation index. The results are illustrated in FIG. 3.

Conclusion of the 2$^{nd}$ Efficacy Trial:

The results obtained show that the adjuvants of oil-in-water emulsion type containing a divalent salt which is the subject of the invention, which may or may not be complexed, are compatible with in ovo vaccination and increase the protection against necrotic enteritis conferred by a subunit antigen. The animals of the adjuvanted groups show, after infection, a higher weight gain, and intestinal lesions which are reduced compared with the animals vaccinated with the nonadjuvanted antigen. They also show antigen-specific serum antibody titers and antigen-specific lymphocyte restimulation indices that are higher than the animals vaccinated with the nonadjuvanted antigen. In this case, the nonadjuvanted vaccine does not make it possible to obtain protection against *C. perfringens* infection.

The invention claimed is:

1. A vaccine for the in ovo vaccination of avian species, comprising at least one antigen and an immune adjuvant,
   the at least one antigen comprising a protein selected from profilin 3-1E from *Eimeiria acervulina*, NetB toxin from *Clostridium perfringens*, or a mixture thereof,
   the immune adjuvant being an oil-in-water emulsion or microemulsion comprising, for 100% of its weight:
      50% to 97% of water,
      1% to 45% of oily adjuvant, the oily adjuvant comprising, for 100% of its weight, 40% to 95% of at least one mineral oil and 5% to 60% of at least one surfactant, and
      0.1% to 10% of at least one divalent salt.

2. The vaccine according to claim 1, further comprising up to 10% of at least one complexing agent.

3. The vaccine according to claim 2, wherein the at least one complexing agent is selected from the group consisting of ethylenediaminetetraacetic acid (EDTA), sodium gluconate, potassium gluconate, sodium polyacrylate, and mixtures thereof.

4. The vaccine according to claim 1, wherein the at least one surfactant is an ethoxylated sugar ester.

5. The vaccine according to claim 1, wherein the vaccine is effective against avian coccidiosis and/or avian necrotic enteritis.

6. The vaccine according to claim 1, wherein the at least one divalent salt is selected from the group consisting of manganese gluconate, calcium gluconate, calcium aspartate, zinc gluconate, iron gluconate, calcium chloride, and mixtures thereof.

7. The vaccine according to claim 1, wherein the at least one antigen is a mixture of profilin 3-1E from *Eimeiria acervulina* and NetB toxin from *Clostridium perfringens*.

8. The vaccine according to claim 1, wherein the at least one mineral oil is a white liquid petroleum jelly of injectable quality.

9. The vaccine according to claim 1, wherein the immune adjuvant comprises, for 100% of its weight:
   80% to 97% of water,
   2% to 10% of oily adjuvant, the oily adjuvant comprising, for 100% of its weight, 50% to 90% of at least one mineral oil and 10% to 50% of at least one surfactant, and
   0.2% to 30% of at least one divalent salt.

10. The vaccine according to claim 9, wherein the at least one surfactant has a Hydrophile-Lipophile Balance (HLB) value equal to 12.

11. A poultry egg, inoculated with the vaccine according to claim 1.

12. The vaccine according to claim 1, wherein the vaccine has been injected into the amniotic cavity of a fertilized poultry egg.

* * * * *